United States Patent [19]

Terao et al.

[11] Patent Number: 6,013,252
[45] Date of Patent: Jan. 11, 2000

[54] METHOD PROMOTING CONCEPTION BY ADMINISTERING IL-8 OR MCAF

[75] Inventors: Toshihiko Terao; Naohiro Kanayama, both of Shizuoka; Masanobu Naruto; Tatsuya Kaneko, both of Kanagawa, all of Japan

[73] Assignee: Toray Industries, Inc., Tokyo, Japan

[21] Appl. No.: 08/817,941

[22] PCT Filed: Aug. 28, 1996

[86] PCT No.: PCT/JP96/02412

§ 371 Date: Jun. 5, 1997

§ 102(e) Date: Jun. 5, 1997

[87] PCT Pub. No.: WO97/07813

PCT Pub. Date: Mar. 6, 1997

[30] Foreign Application Priority Data

Aug. 28, 1995 [JP] Japan ..................... 7-218672

[51] Int. Cl.[7] .......................... A61K 45/05; A01N 37/18
[52] U.S. Cl. .............................. 424/85.1; 424/85.2; 514/2
[58] Field of Search .................... 514/2, 12, 75; 424/85.1, 85.2, 85.4, 85.5; 530/351

[56] References Cited

U.S. PATENT DOCUMENTS

| | | |
|---|---|---|
| 4,879,285 | 11/1989 | O'Neill .................................. 514/75 |
| 5,179,078 | 1/1993 | Rollins et al. ............................ 514/2 |
| 5,624,670 | 4/1997 | Kelly et al. .......................... 424/85.2 |
| 5,646,117 | 7/1997 | Matsushima et al. .................... 514/12 |

OTHER PUBLICATIONS

Anderson et al. "Induction of uterine leukocytosis and its effect on pregnancy in rats" Biology of Reproduction. vol. 21, pp. 1143–1152, 1979.

Biosource International: Products for the study of immunology, 1992, Research Catalog, pp. 2 and 3.

Sigma Biochemicals and Organic Compounds, CAtalog, p. 608, 1993.

*Primary Examiner*—Yvonne Eyler
*Attorney, Agent, or Firm*—Birch, Stewart, Kolasch & Birch, LLP

[57] ABSTRACT

Leukocyte chemotactic factors such as interleukin-8 and MCAF, and inductive substances therefor were revealed to have proconceptive activities. These activities include promoting ovum growth and fertilized ovum implantation, and are exhibited by a sole substance. Accordingly, it has been shown that such substances can be used in drugs concerning medical treatment for infertility, and further, can be used in veterinary and livestock industry fields such as reproduction of industrial animals or species preservation of rare animals.

1 Claim, 3 Drawing Sheets

METHOD PROMOTING CONCEPTION BY ADMINISTERING IL-8 OR MCAF

TECHNICAL FIELD

The present invention relates to a proconceptive agent including a leukocyte chemotactic factor or a substance inducing the leukocyte chemotactic factor as an active principle which has the function of promoting growth of ova and ovarian follicles together with the function of promoting implantation of a fertilized ovum by promoting thickening of endometrium and softening of the interstitial tissue due to edematization. In particular, the present invention relates to a proconceptive medical treatment for mammals.

BACKGROUND ART

In general, the following conditions are considered as essential for establishment of pregnancy:

(1) The existence of sufficient number of sperms having sufficient motility and fertility in an ejaculated seminal fluid;

(2) Normal growth and maturation of ovarian follicles and ova, and discharging of an ovum in ovulation which has fertilizability and cleaving ability;

(3) The form and function of an oviduct maintained normally; and (4) The form and function of a uterus being normal for embryo implantation and maintenance thereof.

In the present situation, however, at least one out of ten married couples is estimated as being unable to satisfy one or more above-described conditions, namely, is infertile. The cases can be broadly classified into 40% of the cases where the causes can be attributed to female factors; 25% of the cases where the causes can be attributed to male factors; 25% of the cases where the causes can be attributed to both female and male factors; and 10% of cases where the causes cannot be clarified.

In respect of such causes, incurable cases as described below are called "absolute infertility": No ova to be discharged are present; the uterus has been extirpated; the husband is azoospermia; or the like. Hitherto, although the case in which both oviducts had been extirpated was regarded as absolute infertility, pregnancy and birth even in such cases have become possible by means of in vitro fertilization (IVF) or embryo transfer (ET). According to development of such an in vitro fertilization or embryo transfer method, pregnancy in cases such as atretic oviduct or oligozoospermia, in which pregnancy had been impossible, has become possible. The ratio of pregnant cases by in vitro fertilization to the total number of in vitro fertilization operations is still as low as approximately 20 to 30%, and the ratio of the cases resulting in birth is only 5 to 10%. Concerning such low ratios, implantation failure in returning fertilized ova to the uterus is considered as a cause. In addition, implantation disability is pointed out as possibly occupying a high percentage of the causes for unaccountable infertility or so called functional infertility.

Although artificial insemination is also frequently performed in animals other than human beings, the conception rate and birth rate therein are not necessarily satisfactory. In particular, when such operations are performed for preservation and reproduction of rare animals, such low rates are problems since there exists a temporal limitation due to the high ages of the remaining animals or the like. Similar to cases of human beings, it is considered that such low rates may be attributed to a failure in sufficiently satisfying the above-described conditions in the steps for establishing pregnancy.

Through a series of developmental stages, an ovum is formed from an oocyte which has been derived from an oogonium. In mammals, an oogonium stops dividing just before or just after birth, and transforms into an oocyte which is a meiotic-type cell. In the latter stage of the prophase of the first meiosis, the oocyte comes into a stationary phase, and changes in its chromosomes do not progress (interphase of the first meiosis). At this time, the nucleic volume of the oocyte increases, and such an oocyte is called a "protoblast" (or "germinal vesicle"). The oocyte, then, restarts meiosis in response to gonadotropin secreted from the pituitary gland. In many mammals, the meiosis is restarted in an ovarian follicle before ovulation; the protoblast is then broken (germinal vesicle breakdown); a first polar body is released through the metaphase, the anaphase and telophase of the first meiosis; and the chromosomes stop changing in the metaphase of the second meiosis (interphase of the second meiosis). According to fertilization, the second meiosis restarts, a second polar body is released, and the meiosis is thus completed ["Jikken Seishoku-Seirigaku no Tenkai (Development of Experimental Reproductive Physiology)", vols. 11 to 16 edited by Yosisuke Suzuki, and published by Soft Science Co., Ltd, 1982]. Investigations on ovum maturation have been conducted principally using in vitro culture systems while employing the following three methods depending on the purposes of experiments.

(1) Culturing oocytes harvested from ovarian follicles under several conditions. This method is employed for analysis of factors influential upon ovum maturation.

(2) Culturing oocytes together with theca cells, or culturing oocytes in a conditioned medium based on ovarian follicles. This method is employed for analyzing influences by theca cells.

(3) So called "organ culture" in which ovarian follicles including oocytes are externally cultured. This method is employed for analysis of factors influential upon ovum maturation passing through or with intervention of thecae.

As the first step for conception, an adequate maturation process for a vital ovum is essential. The term "ootid" means an ovum which can release a second polar body in response to fertilization, and thereby complete fertilization as well as meiosis (namely, having fertilizability), and which can develop in response to fertilization stimulation (namely, having developmental potency).

The latter step for conception includes the activity of a fertilized ovum traveling through an oviduct toward the inner surface of a uterus for implantation. When a disability concerning either of the above-described steps is present on the female side, conception cannot be achieved or can be achieved only with a markedly low degree of probability though depending on the degree of the disability. Implantation is understood as an adhesion phenomenon between a fertilized ovum and endometrium. Upon implantation, endometrium as a receiver for a fertilized ovum should sufficiently thicken, and the interstitial tissue should be edematized to be soft. It was reported that implantation of a fertilized ovum rarely occurs if the interstitial tissue does not swell in the ovulation period. In the above-described infertility cases in human beings, several therapeutic treatments are performed depending on the causes thereof. For example, for oligozoospermia or azoospermia, sperms manually obtained are injected on an ovulation day into the uterus lumen or the oviduct in an attempt to achieve natural fertilization in the oviduct. Nowadays, a just ejaculated seminal fluid is not used for fear of bacterial infection, and therefore, washed and condensed sperms are used. In many cases, however, a few to tens of attempts at insemination are required until conception is achieved, and unsuccessful implantation is considered as one reason for such requirement.

Further, in vitro fertilization and embryo transfer are performed in cases such as atretic oviduct or oligozoospermia where other therapeutical treatments are not effective, wherein ova taken out of a body are inseminated with sperms, and after fertilization, divided and grown embryos are transvaginally transferred on the inner surface of a uterus. In practice, the operation comprises the following significant steps: (1) Induction of superovulation, and determination of a ovum collection period; (2) an operation for ovum collection; (3) supplemental culturing for ovum maturation; (4) collection of satisfactory sperms and capacitation; (5) in vitro fertilization; (6) culturing of the fertilized ova; (7) embryo transfer; and (8) luteal phase management. Without completion of these steps, pregnancy cannot be expected to occur. Since the endocrine system is not physiologically natural in such an estrus cycle with superovulation induction, hormonotherapy as an luteal phase management, such as administration of progesterone or the like for approximately one week after the embryo transfer, is performed for luteinization, namely thickening of endometrium and softening of the interstitial tissue. Nevertheless, the pregnancy rate is unsatisfactory, as described above, and therefore, there are demands for a further improved method.

As a modification of in vitro fertilization/embryo transfer, a related art generically called "assisted reproductive technology" has been developed. This technology includes intraoviduct zygote transplantation in which in vitro fertilization is performed, and then fertilized ova, either before division or after division and growth, are transplanted into an oviduct; and intraoviduct gametes transplantation in which collected ova in an early phase are transplanted together with sperms into an oviduct. Although these are methods which provide conditions closer to the physiologically natural process of pregnant, problems concerning implantation of a fertilized ovum has not yet been solved, and there is room for improvement.

Meanwhile, inflammation reactions as bioprotective reactions are observed not only in bacterial or viral infections and injuries, but also in tissue damage due to autoimmune reactions. At this time, specific peripheral leukocytes infiltrate into the inflammatory region. For leukocyte migration on such occasions, chemokines (chemotactic factors) play an important role. Interleukin-8 is one of such chemokines, and its excessive production is considered as a cause of several inflammatory diseases.

Interleukin-8 has been reported to be produced from several types of cells such as fibroblasts and several tumor cells as well as hemocytes such as monocytes, macrophages, and lymphocytes in response to stimulation by IL-1, TNF, LPS, or the like. Accordingly, interleukin-8 is deduced to be an important mediator for acute inflammation, and abnormal production is considered relating to some diseases. Examples of such diseases include rheumatoid arthritis, gouty arthritis, asthma, septicemia, immunological vasculitis, hepatitis, and pyelonephritis. The activity of interleukin-8 in such diseases has, however, been known only at a basic science, and the mechanism of how it relates to progress in pathologic processes of such diseases has not yet been clarified. Interleukin-8 is a chemokine which has the functions of causing chemotaxis of neutrophils and lymphocytes, and activating neutrophils and other mononuclear leukocyte or the like. The term "chemokine" means a bioactive substance (or cytokine) which has an activity of causing chemotaxis. Interleukin-8 is a protein comprising 69 to 77 amino acids. The number of amino acids alters depending on the situation since the N terminus processed with intra- or extracellular enzymes. At first, interleukin-8 was reported in the name of MDNCF (K. Matsushima, et al., *J. Exp. Med.*, 167, 1883, 1988), after that, it was also found by other researchers and named differently, and the name was unified as "interleukin-8" (C. G. Larsen, et al., *Science*, 243, 1464, 1989). Interleukin-8 belongs to the CXC chemokine family, the members of which have similar amino acid numbers and similar cysteine residue configurations. "CXC chemokine family" is a generic term for a group of low-molecular weight proteins which mutually have amino acid homologies of approximately 30%, and the same four cysteine residue positions. Structural analogues of interleukin-8 such as γIP-10, GRO (α, β, γ), PF-4, and NAP-10 are known as proteins belonging to this family other than interleukin-8 (N. Mukaida, et al., *Microbiol. Immunol.*, 36, 773, 1992). Proteins of the CXC chemokine family are characterized by having a N terminus amino acid sequence in which two cysteine residues are bonded with an intervening amino acid residue. "CXC chemokine" is also called "β chemokine" (J. J. Oppenheim, et al., *Annual. Rev. Immunol.*, 9, 617, 1991).

Monocyte chemotactic and activating factors (hereinafter referred to as MCAF) have been reported to be produced from several types of cells such as fibroblasts, endothelial cells, smooth muscle cells and several tumor cells as well as hemocytes such as monocytes, macrophages, and lymphocytes in response to stimulation by IL-1, TNF, IFN-γ, LPS, or the like. Additionally, the monocyte chemotactic and activating factor is also called MCP-1 (monocyte chemoattractant protein-1) or GDCF (glioma-derived monocyte chemotactic factor), and is a protein comprising 76 amino acids and having 4 cysteine residues. Reports have been made concerning identification and gene cloning of MCAF, MCP-1 or GDCF (K. Matsushima, et al., *J. Exp. Med.*, 169, 1485, 1989; Y. Furutani, et al., *Biochem. Biophys. Res. Commun.*, 159, 249, 1989; E. R. Robinson, et al., *Proc. Natl. Acad. Sci. USA*, 86, 1850, 1989; and T. Yoshimura, et al., *FEBS Letters*, 244, 487, 1989). Hereinafter, in the present invention, "MCAF" is used as a generic term also including MCP-1 and GDCF.

MCAF belongs to the CC chemokine family, the members of which have similar amino acid numbers and similar cysteine residue configurations. "CC chemokine family" is a generic term for a group of low-molecular weight proteins which mutually have amino acid homologies of approximately 30%, and the same four cysteine residue positions. Structural analogues of MCAF such as RANTES, LD78, ACT2, I-309, MCP-2 and MCP-3 in human beings, or JE, MIP-1 α, MIP-1 β, and TCA-3 in mice are known as proteins belonging to this family other than MCAF (N. Mukaida, et al., *Microbiol. Immunol.*, 36, 773–789, 1992). Proteins of the CC chemokine family are characterized by having a N terminus amino acid sequence in which two cysteine residues are bonded in series. "CC chemokine" is also called "β chemokine" (J. J. Oppenheim, et al., *Annual. Rev. Immunol.*, 9, 617, 1991).

The present inventors have reported that administration of an interleukin-8 suppository to a rabbit can cause cervical ripening (El Maradny, et al., *Am. J. Obstet. Gynecol.*, 171, 77, 1994). Cervical ripening is essential for parturition, and cervical ripening incompetency is the principal cause of today's dystocia. By local administration of interleukin-8, inflammatory cells such as neutrophils migrate into the cervix to release collagenase, elastase or the like which degrades collagen in the interstitial tissue, increase the content of water in the interstitial tissue, and thus cervical ripening takes place. However, effects of interleukin-8 or MCAF upon the steps of oogenesis, ovum maturation, fertilization, and achievement of conception have not yet been known.

The following are known as examples of means for improving conception rate: Inductive substances for resumption of the first meiosis such as cyclic AMP, calcium ions, prostaglandins, cholera toxins, and forskolin; follicle stimulating hormone (FSH) or the like for attempting follicular maturation; estrogen or the like for attempting to provide developmental potency for fertilized ova; and luteal phase management using a steroid agent or the like for attempting to achieve implantation of fertilized ova.

According to these means, however, a satisfactory pregnancy rate may not be achieved, or some agents cannot actually be used or can be used with limitations due to side effects inherent in the uses thereof.

DISCLOSURE OF INVENTION

The present invention relates to a proconceptive agent including a leukocyte chemotactic factor or an inducer thereof as an active principle.

BRIEF DESCRIPTION OF THE DRAWINGS

FIG. 2 indicates the results of Example 5.

BEST MODE FOR CARRYING OUT THE INVENTION

Figure 1:
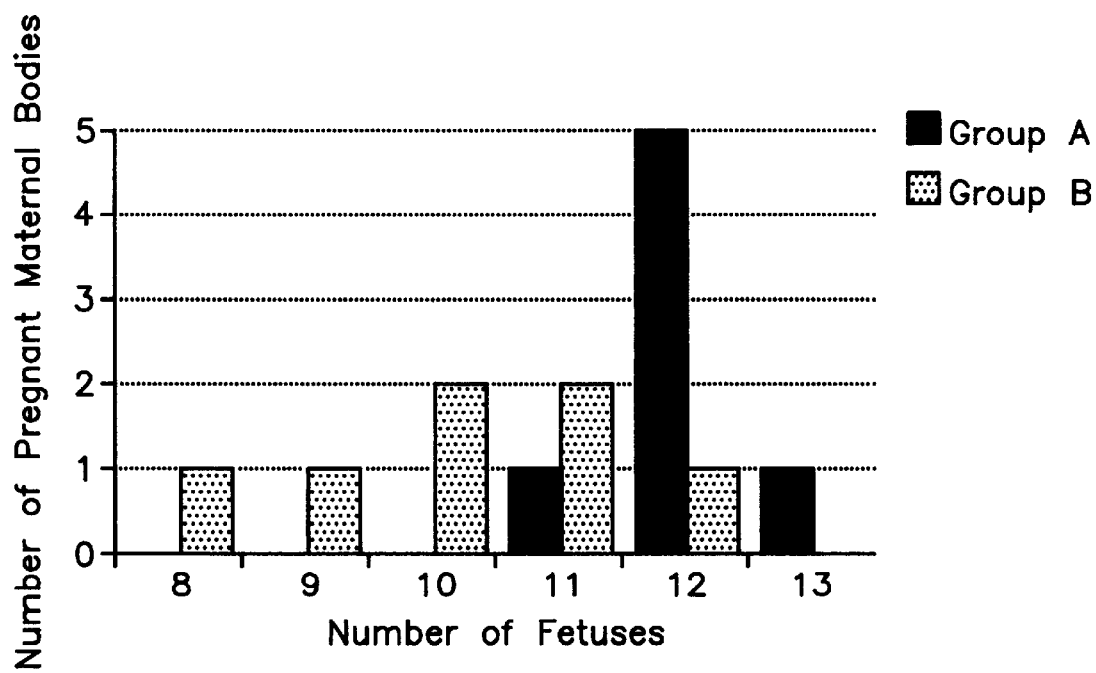
FIG. 1 shows the results of Example 1. Interleukin-8 is administrated to group A while saline is administrated to group B. The horizontal axis indicates the number of fetuses per maternal body while the vertical axis indicates the number of maternal bodies which had fetuses of the number indicated by the horizontal axis.

The present inventors gave attention to the facts that cytokines are involved in the ovulation process for pregnancy, and that the endometrium is in a physiological inflammatory state during the process of fertilized ovum implantation. As a result, we found that interleukin-8 or MCAF, which cause migration and activation of leukocytes, exhibit suitable effects in each step for achieving pregnancy (growth of ovarian follicles, resumption of meiosis, implantation of a fertilized ovum, and others), and administration solely of such an agent can improve conception rate. Based on these findings, the Inventors accomplished the present invention. In the present invention, the proconceptive action includes both steps for promoting maturation of unfertilized ova, and promoting implantation of fertilized ova.

Promotion of fertilized-ovum implantation, which is the latter step of the present invention, comprises local administration of a leukocyte chemotactic factor to cause a biological reaction aiming at local migration of leukocytes. The term "leukocyte chemotactic factor" is a generic term for all substances capable of inducing leukocyte chemotaxis, and includes several substances produced in some microorganisms or inflammatory tissues. Examples of such substances include interleukin-8 and chemokines analogous thereto. The chemokines analogous to interleukin-8 include chemokines belonging to the interleukin-8 family, namely, CXC chemokines (such as GCP-2, GRO$\alpha$, GRO$\beta$, GRO$\gamma$, PF4, NAP-2, ENA-78, IP-10, MIG, PBP, CTAP-III, SDF-1$\alpha$, and SDF-1$\beta$); and chemokines belonging to the MCAF (or MCP-1, i.e. monocyte chemotactic and activating factor or monocyte chemoattractant protein-1) family, namely, CC chemokines (such as hMIP-1$\alpha$, hMIP-1$\beta$, MCP-2, MCP-3, RANTES, and I-309) (Drug & Development, 7, 57–65, 1996). MCAF is known to cause physiological inflammation by causing migration and activation of monocytes and macrophages, and secondary production of interleukin-8 during this process has been observed. Accordingly, MCAF and analogues thereof having such physiological activities can also be used for promoting fertilized-ovum implantation since they can indirectly thicken the endometrium and soften the interstitial tissues. From among such substances, interleukin-8 and MCAF are preferably used.

Additionally, the following substance may also be preferably used: Substances inducing production of a leukocyte chemotactic factor, such as interleukin-1, interferon $\gamma$, tumor necrosis factors (TNF); platelet activating factors (PAF) having physiological activities analogous to chemokines and serving as leukotactic substances; and LPS, which is one endotoxin.

Interleukin-8 and MCAF can be obtained from natural sources according to ordinary isolation/purification methods such as column chromatography. Alternatively, those obtained by culturing cells which produce them, chemical synthesis, or gene recombination technology can also be used. Such production methods are disclosed in Japanese Laid-open Patent Publications(Kohyo) No. 3-505037 and No. 4-500156, Japanese Unexamined Patent Publication (Kokai) No. 2-207788, and others. Additionally, commercially available interleukin-8 and MCAF manufactured by companies such as Oncogene Science (USA) and PEPRO-TEC (USA) can also be used.

Further, the origin of the interleukin-8 or MCAF to be used is not limited to human beings or animals which are the subjects to be administered. Interleukin-8 or MCAF species derived from dissimilar animal origin can be used so long as the problems concerning undesired effects upon the human or animal body to be administered, such as hyperimmune response, can be overcome. Moreover, those having the same amino acid sequences except for one or more amino acid residues which are replaced, inserted, deleted, and/or modified; and peptides each comprising a part of the amino acid sequence for the objective structure can also be used for working of the present invention so long as they exhibit the desired activity.

Incidentally, interleukin-8 or MCAF can be solely administrated directly into the uterus, and in addition, combined formulations comprising both thereof or ingredients having identical or analogous effects can also be administrated.

Additionally, ordinarily used excipients, binders, lubricants, tinctions, stabilizers, and others can be added to the medicine of the present invention in the preparation process. The dosage form of the proconceptive agent in relation to the present invention is not especially limited so long as the object of the present invention can be achieved thereby, and thus, the dosage form can be a liquid type such as a liquid formulation to be sprayed in the uterus; a semi-solid type such as an ointment, a cream, or a gel formulation; and a solid type such as a virginal tablet, a vaginal capsule, a pessary, or a vaginal suppository. Further, when a formulation such as a liquid or semi-solid formulation which can be applied onto a uterine cervix dilator is employed, administration through such a dilator can be performed. Hereupon, the action "application" includes not only application of the medicine onto the surface of such a dilator or the like, but also immersion of the medicine onto such a dilator or the like through a immersing means properly provided thereon. In addition, intraperitoneal administration through the Douglas pouch or the like can be carried out. As a matter of course, dosage forms suitable to intraperitoneal, intravenous, oral, or transpulmonary administration can be employed for achieving the purpose of the present invention, as typically shown in examples of the present invention described below.

In preparation of the above-described formulations, additive ingredients generally used in drug formulations can be combined to achieve the objective dosage forms.

Examples of such ingredients include animal or vegetable oils (such as soybean oil, coconut oil, beef tallow, and synthetic glyceride); hydrocarbons (such as liquid paraffin, squalene, and solid paraffin); ester oils (such as octyl dodecyl myristate and isopropyl myristate); higher alcohols (such as cetosterial alcohol and behenil alcohol); silicon resins; silicon oils; surfactants (such as polyoxyethylene fatty acid esters, sorbitan fatty acid esters, glycerol fatty acid ester, polyoxyethylene fatty acid esters, polyoxyethylene hardened castor oil, and polyoxyethylene polyoxypropylene block copolymer); water-soluble polymers (such as hydroxyethyl cellulose, polyacrylic acid, carboxyvinyl polymer, polyethylene glycol, polyvinyl pyrrolidone, and methyl cellulose); alcohols (such as ethyl alcohol, and isopropyl alcohol); polyhydric alcohols (such as glycerol, propylene glycol, dipropylene glycol, and sorbitol; saccharides (such as glucose and sucrose); inorganic powders (such as silicic acid anhydride, aluminum magnesium silicate, and aluminum silicate); and purified water. For pH adjustment, compounds such as described below can be used: Inorganic acids (such as hydrochloric acid and phosphoric acid); alkali metal salts of inorganic acids (such as sodium phosphate); inorganic bases (such as sodium hydroxide); organic acids (such as lower fatty acids, citric acid, and lactic acid); alkali metal salts of organic acids (such as sodium citrate and sodium lactate); and organic bases (such as arginine and ethanolamine). As occasion demands, preservatives, antioxidants, and others can also be added. In practice, such additives are selected, optionally or in combination, from among the above-described compounds depending on the dosage form of the medicine for the object disease of the present invention, though, needless to say, not limited to the above-described compounds. Additionally, formulations satisfying the object of the present invention can readily be obtained by mixing the active principle in a commercially available suppository basis (such as Witepsol manufactured by Mitsuba Co., Ltd.). Further, the material and shape of the uterine cervix dilator to be used in the present invention is not especially limited so long as the dilator can be used for the desired object. Examples of such dilators include dilators comprising a plant such as *Laminaria japonica*; dilators comprising conventionally used synthetic resins (water-absorptivity, thermoplasticity, and water-bloating tendency of the resin do not matter, and whether the base material is spongiform or fibrous does not matter either); and dilators comprising polymeric absorbents.

Interleukin-8 and MCAF are administrated at, for example, 1 pg/kg to 10 mg/kg, preferably 100 pg/kg to 1 mg/kg, and more preferably 1 ng/kg to 10 µg/kg though it depends on the age of the woman as an administration subject, the state of reproductive system such as ovary function and degree of thickening in the endometrium, and health conditions of the maternal body. The above-described ranges are not directed to any limitation, and interleukin-8 and MCAF may be contained in amounts necessary to exhibit the desired pharmacological effects. Further, the dosages of other leukocyte migration factors or inducers therefor should finally be determined by the medical staff.

The present invention provides a usage of the compound of the present invention in relation to pregnancy. Further, the present invention provides a usage of the compound of the present invention in relation to internal, surgical, or diagnostic treatments for ovum maturation and promotion of fertilized ovum implantation. Accordingly, the present invention can be utilized in human beings as described below, though not limited to such uses.

(1) In infertility cases with no abnormalities both in sperm and ova, such as functional infertility, the compound of the present invention can be administrated before or after copulation in an attempt to promote the growth of ova and/or to promote fertilized ovum implantation, thereby enhancing the possibility of pregnancy or conception.

(2) In infertility cases where the causes are attributed to either or both male and/or female factors, or infertility cases where the causes are unclarified, the compound of the present invention can be used for an in vitro ovum treatment, and/or administrated to the maternal body at the vagina, uterus and neighboring areas thereof before and after, or at the same time as such a treatment in artificial insemination or human being in vitro fertilization in an in vitro fertilization/embryo transfer method or a modification method thereof such as intraoviduct zygote transplantation and intraoviduct gametes transplantation, in an attempt to promote growth of ova and/or to promote fertilized ovum implantation, thereby enhancing the possibility of pregnancy or conception.

The invention described above is applicable to animals other than human beings. Specifically, a proconceptive agent containing interleukin-8 or MCAF as an active principle is used for in vitro treatment of ova collected beforehand, and/or directly administrated to the animal for ovum growth, or as a therapy, operation or treatment concerning a fertilized ovum implantation process. In other words, such an agent can be used for the purpose of reproduction of domestic animals such as cattle, horses, and pigs; companion animals such as dogs and cats; and wild animals such as giant pandas, tigers, and rhinoceroses. Reproduction of these animals is beneficial to mankind since it leads to low-cost provision of meat and milk from superior domestic animals, maintenance of stocks exhibiting excellent characteristics, and preservation of rare animals. For animal use, the compound of the present invention can be used as described below, though not limited to such uses.

(1) The compound of the present invention is administrated before or after copulation of animals in an attempt to promote the growth of ova and/or to promote fertilized ovum implantation, thereby enhancing the pregnancy or conception rate.

(2) The compound of the present invention is used for an in vitro treatment of ova collected from the maternal body, and/or administrated to the maternal body at the vagina, uterus and neighboring areas thereof on artificial insemination or in vitro fertilization of an animal in an attempt to promote growth of ova and/or to promote fertilized ovum implantation, thereby promoting achievement of pregnancy or conception.

EXAMPLES

The effects of the present invention are shown with reference to examples below. The following examples are described only for illustration, and should not be understood as limitations in any respect. Incidentally, the interleukin-8 and MCAF provided by Dr. K. Matsushima were used in the following examples (K. Matsushima, and J. J. Oppenheim, CYTOKINE, 1, 2–13, 1989).

Example 1

Promoting Effect of Interleukin-8 on Fertilized Ovum Implantation

The following experiment using rats was conducted in order to evaluate the effect of interleukin-8 on fertilized ovum implantation.
(1) Method
Fourteen Wister rats (clean grade, female, 10-week-old) were divided into two groups, A and B, each comprising 7 rats. The female rats of group A (interleukin-8 dosed group) were placed in cages one by one, and male Wister rats (clean grade) were then placed in the same cages one by one. Every morning, whether or not mating had occurred was confirmed according to vaginal smear observation, and the rat couples were separated when completion of mating was confirmed. Immediately after mating confirmation, the female rats were intraperitoneally dosed with 10 μg/0.2 ml saline of interleukin-8 each, and observed for 10 days. On the tenth day, the female rats were dissected, and the number of fetuses were determined. Similarly, the female rats of the group B (control group) were placed in cages one by one, and male Wister rats (clean grade) were then placed in the same cages one by one. Every morning, whether mating had occurred or not was confirmed according to vaginal smear observation, and the rat couples were separated when completion of mating was confirmed. Immediately after mating confirmation, the female rats were intraperitoneally dosed with 0.2 ml of saline each, and observed for 10 days. On the tenth day, the female rats were dissected, and the number of fetuses were determined.
(2) Results
The rat uterus is bicornuate, and in general, the number of fetuses per female rat is approximately 9 to 11. The number of fetuses in group A was 12±0.6 while that in group B was 10±1.4, and accordingly, an increase in the number of fetuses was observed in the group dosed with interleukin-8 ($P<0.068$). The histograms of groups A and B are shown in FIG. 1. In the group dosed with interleukin-8, every maternal rat except for one rat got pregnant with 12 or more fetuses, and accordingly, an improvement in conception rate was clearly recognized. Incidentally, miscarriage due to administration of interleukin-8 was not observed in any rats.

Example 2

Observation of Histological Changes in Rats Dosed with Interleukin-8

The following experiment using rats was conducted in order to histologically observe the effects of interleukin-8 on the endometria.
(1) Method
Six Wister rats (clean grade, female, 10-week-old) were divided into two groups, A and B, each comprising 3 rats. Each rat in group A (interleukin-8 dosed group) was intraperitoneally dosed with 10 μg/0.2 ml saline of interleukin-8 each, and 12 hours later, the uterus and the endometrium were visually inspected. These tissues were then fixed with a 10% neutral buffered formalin and stained with hematoxylin/eosin, and histological changes were microscopically observed. Similarly, each rat in group B (control group) was intraperitoneally dosed with 0.2 ml of saline alone, and 12 hours later, the uterus and the endometrium were visually inspected. These tissues were then fixed with a 10% neutral buffered formalin and stained with hematoxylin/eosin, and histological changes were microscopically observed.
(2) Results
The endometrium of each rat in group A was markedly swollen to be edematous, and thickening was also recognized. This state of the endometrium is similar to that of a human being in case of fertilized ovum implantation. On the other hand, changes such as swelling or thickening of the endometrium could not be observed in group B (control group).

Example 3

Observation of Histological Changes in the Endometria of Rabbits Dosed with Interleukin-8

The following experiment using rabbits was conducted in order to histologically observe the effects of interleukin-8 on the endometria.
(1) Method
Six New Zealand white rabbits (female, body weight of 3 kg) were divided into two groups, A and B, each comprising 3 rabbits. Each rabbit of group A (interleukin-8 dosed group) was intravaginally dosed with a suppository every day for 3 days, wherein the suppository had been prepared by adding 1 μg of interleukin-8 to 100 μl of 50° C.-melted Witepsol W35 (Mitsuba Co., Ltd.), and by cool-solidifying the resultant at 4° C. On the fourth day from the start of the experiment, dissection was performed, and the isolated uteri were visually inspected and then fixed with a 10% neutral buffered formalin. The obtained tissue sections were stained with hematoxylin/eosin, and histological changes were microscopically observed. Similarly, each rabbit in group B (control group) was intravaginally dosed with a suppository which comprised the base alone and was prepared in the same manner as for the group A, and subjected to dissection and observation of histological changes in the same manner as for group A.
(2) Results
Similar to the results of Example 2, the endometrium of each rabbit in group A was markedly swelled to be edematous, and thickening was also recognized. It was proven that administration of the drug in the manner of a suppository could also induce endometrial changes similar to those shown in fertilized ovum implantation. On the other hand, such changes could not be observed at all in group B (control group).

Example 4

Observation of Histological Changes in Rats Dosed with MCAF

The following experiment was conducted in order to histologically observe the effects of MCAF on the endometria of rats.
(1) Method
Six Wister rats (clean grade, female, 10-week-old) were divided into two groups, A and B, each comprising 3 rats. Each rat in group A (MCAF dosed group) was intraperitoneally dosed with 10 μg/0.2 ml saline of MCAF, and 12 hours later, the uterus and the endometrium were visually inspected. These tissues were then fixed with a 10% neutral buffered formalin and stained with hematoxylin/eosin, and histological changes were microscopically observed. Similarly, each rat in group B (control group) was intraperitoneally dosed with 0.2 ml of saline alone, and 12 hours later, the uterus and the endometrium were visually inspected. These tissues were then fixed with a 10% neutral buffered formalin and stained with hematoxylin/eosin, and histological changes were microscopically observed.

(2) Results

The endometrium of each rat in the group A was markedly swelled to be edematous, and thickening was also recognized. This state of the endometrium is similar to that of a human being in case of fertilized ovum implantation. On the other hand, changes such as swelling or thickening of the endometrium could not be observed in the group B (control group).

Example 5

Effect of Interleukin-8 (in vitro Administration) on Growth of Ovary Oocytes (1) Method This experiment was carried out according to a basic procedure as follows: Twelve Wister rats (clean grade) which were sexually immature (27- to 28-day-old) were each dosed with 15 international units of pregnant mare serum gonadotropin (PMSG, Sigma, St. Louis, Mo.), and 48 hours later, intraperitoneally dosed with 15 international units of human chorionic gonadotropin (hCG, Sigma, St. Louis, Mo.) or 17 µg of interleukin-8.

After the administration of hCG or interleukin-8, ovary extirpation was periodically performed, and the isolated ovaries were fixed with 3.5% paraformaldehyde (pH 7.4) for 24 hours. The resultant was then dehydrated with a series of increasing concentration alcohol solutions, embedded in paraffin, sliced into sections of 4 µm in thickness, deparaffinized, hydrated, and stained with hematoxylin/ eosin. The stained sections were subjected to microscopic examination for observation of the nucleic stage in meiosis and cumulus-oocyte complexes in Graafian follicles. Resumption of meiosis was confirmed according to breakdown of the protoblast (germinal vesicle) from each oocyte.

(2) Results

Figure 2A:
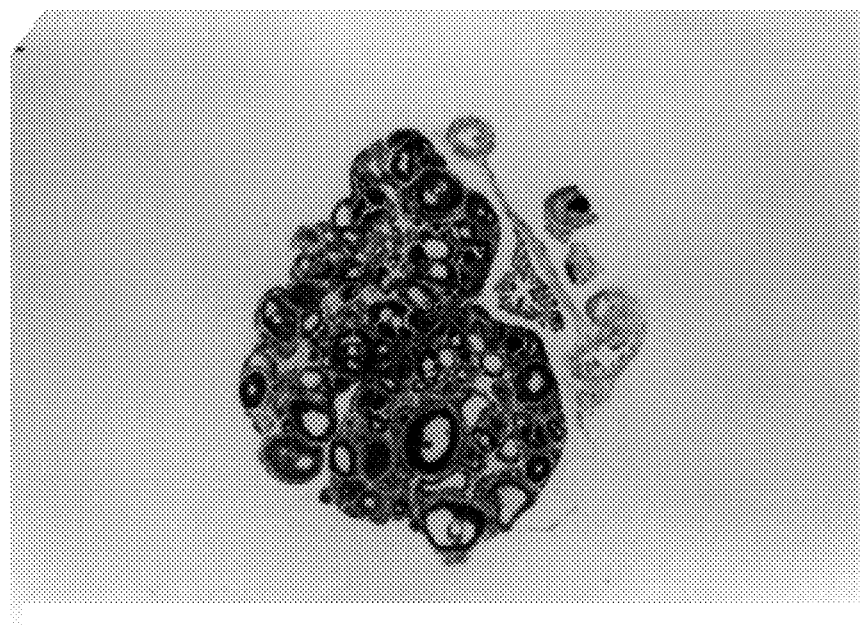
FIG. 2(A) shows a hematoxylin/eosin-stained section of an ovary as a control (at 0 hours and without drug administration)
Figure 2B:
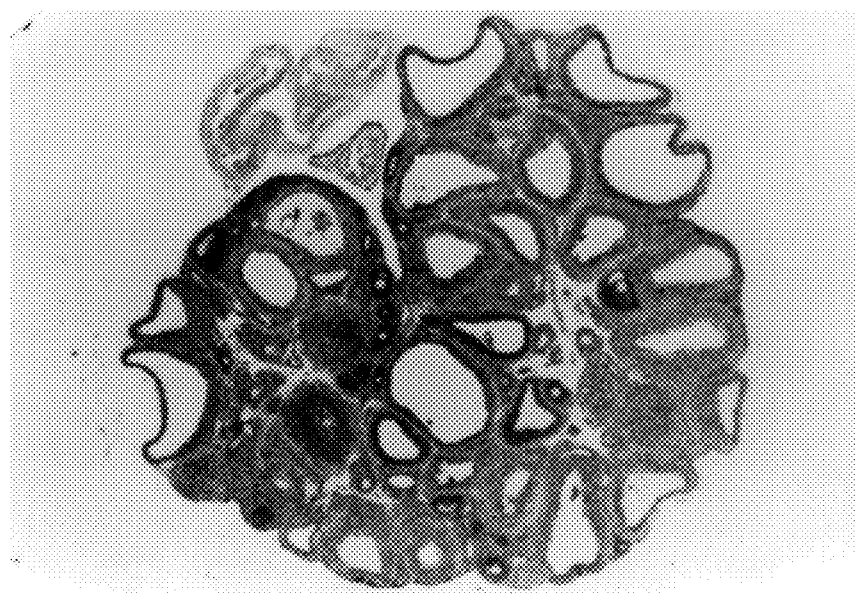
FIG. 2(B) shows a hematoxylin/eosin-stained section of an ovary 10 hours after the administration of hCG.
Figure 2C:
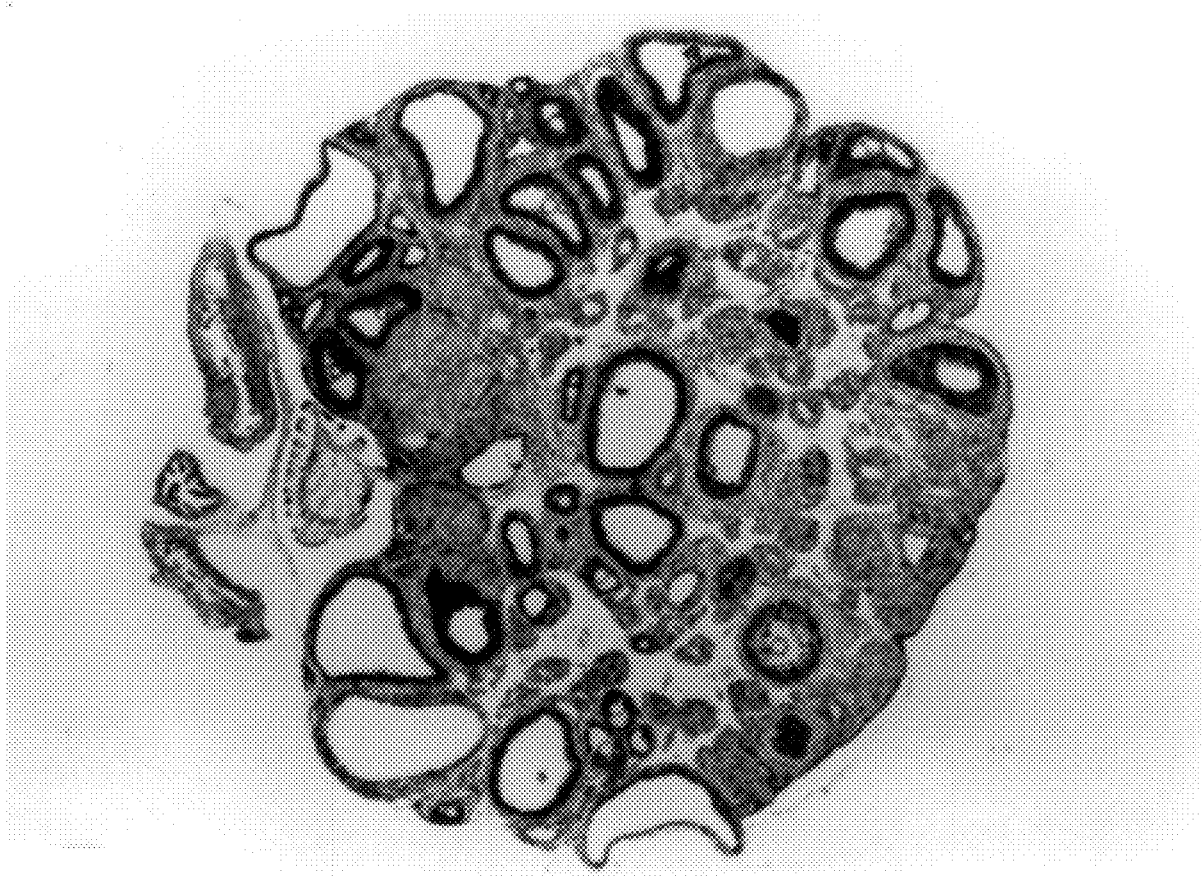
FIG. 2(C) shows a hematoxylin/eosin-stained section of an ovary 10 hours after administration of interleukin-8. The bars in these pictures indicate 200 $\mu$m.

FIG. 2 contains section views of the maximum diameter parts of isolated ovaries. Before hCG administration, all oocytes in normal Graafian follicles had normal germinal vesicles (FIG. 2A). Ten hours after hCG administration, the germinal vesicles disappeared, and most of the oocytes had extruded first polar bodies. As is shown FIG. 2B and obvious when compared with the control, ovarian follicles of the rats had markedly developed with hCG administration. These results are consistent with results which have been reported previously. On the other hand, ovarian follicles also grew by administration of interleukin-8 instead of hCG to a degree similar to that by hCG administration (FIG. 2C). With hCG administration, 72% of germinal vesicles came into breakdown while 54% of germinal vesicles came into breakdown with interleukin-8 administration.

Additionally, the number of oocytes and the number of germinal vesicle breakdowns after hCG or interleukin-8 administration are shown in Tables 1 and 2.

TABLE 1

Germinal Vesicle Breakdown in Rat Graafian Follicle Ova after PMSG and hCG Administration

| Time after hCG Administration (hour) | Number of Observed Ova | Germinal Vesicle Breakdown Number | Percentage |
|---|---|---|---|
| 0 [n = 1] | 51 | 2 | 4 |
| 10 [n = 3] | 114 | 82 | 71.9 |
| 20 [n = 1] | 48 | 25 | 52 |

The examined graafian follicles were 0.4 mm or more in long axis, and 0.3 mm or more in short axis. The letter n represents the number of ovaries.

TABLE 2

Germinal Vesicle Breakdown in Rat Graafian Follicle Ova after PMSG and IL-8 Administration

| Time after IL-8 Administration (hour) | Number of Observed Ova | Germinal Vesicle Breakdown Number | Percentage |
|---|---|---|---|
| 4 [n = 1] | 38 | 2 | 5.3 |
| 10 [n = 3] | 106 | 57 | 53.8 |
| 20 [n = 3] | 104 | 24 | 23 |

The examined graafian follicles were 0.4 mm or more in long axis, and 0.3 mm or more in short axis. The letter n represents the number of ovaries.
IL-8: Interleukin-8

As is obvious from the results, interleukin-8 has an activity of causing equivalent ovum maturation to hCG; and promoting resumption of meiosis in a mature follicle, germinal vesicle breakdown, first polar body release through the metaphase, anaphase and telophase of the first meiosis, and the progress from the metaphase of the second meiosis to the interphase of the second meiosis.

Example 6

Effects of Interleukin-8 in vitro on Cumulus-oocyte Complex Expansion (1) Method Rats were dosed with PMSG, and 48 hours later, the ovaries were isolated. The cumulus-oocyte complexes were then individually harvested from Graafian follicles by puncture, dispersed in Eagle's Minimum Essential Medium (MEM, Nissui Pharmaceutical Co., Ltd., Japan), recovered using a micropipette, and transferred into 50 µl of MEM, the surface of which was covered with a silicon oil (Aldrich Chemicals Co., USA) to prevent evaporation. The resultant was then incubated in a medium without addition of serum at 37° C. for 20 hours in an atmosphere of 5% carbon dioxide gas and 95% air. Interleukin-8 was added in an amount of 100 ng/ml.

(2) Results

In the presence of serum, a cumulus-oocyte complex will exhibit cumulus expansion through in vitro incubation for approximately 20 hours. On the other hand, it is known that the cumulus expansion reaction does not occur in the absence of serum, and this fact was reproduced in this experiment. Nevertheless, cumulus expansion or mucus secretion was induced by incubation with addition of interleukin-8 even in the absence of serum. Accordingly, interleukin-8 has been revealed to directly act on a cumulus-oocyte complex and exhibit effects as described above.

Example 7

Distribution of Interleukin-8 in the Ovarian Tissue and Ovarian Cells

Immunostaining at tissue and cell level was performed in order to clarify distribution and production sites of interleukin-8 in the ovary.

(1) Method

From Wister rats (clean grade), ovaries were isolated and made into serial sections of 4 μm in thickness according to the process in Example 5. These sections were then incubated together with polyclonal rabbit antibodies raised against rat interleukin-8 (10 mg/ml) at 4° C. overnight. Subsequently, the sections were washed with phosphate buffered saline (pH 7.2, hereinafter referred to as PBS) 5 times, and incubated together with a 100-fold-diluted fluorescein isothiocyanate-rabbit immunoglobulin G conjugate solution at 23° C. for 3 hours in a dark place. The sections were then washed with PBS again, and mounted with a glycerin-PBS (1:1, v/v) solution to be subjected to observation with a fluorescence microscope (Axiophoto, Carl Zeiss, Germany).

Preparation of granulosa cells and thecal interstitial cells was carried out according to the method of Li, Y-X, et al. (Li, Y-X, et al., *Mol. Cell. Endocrinol.*, 54, 221, 1987). The procedure will be briefly described below. A subject ovarian follicle was punctured using a 28 gauge subcutaneous injection needle, and the contents were removed and dispersed into MEM. Granulosa cells without cumulus-oocyte were collected by centrifugation. The remaining ovary was sufficiently punctured using the same needle, and washed several times to remove residual granulosa cells. Afterward, the ovarian tissue was incubated in a 0.08% collagenase solution at 37° C. for 5 min. The dissociated cells were discarded, and the ovarian tissue fragments were further incubated in a 0.4% collagenase solution at 37° C. for 1 hour to collect thecal interstitial cells. The obtained cells were dispersed in MEM containing 5% fatal bovine serum at a density of $1 \times 10^5$ cells/ml, seeded in a 4-well Labtech chamber (Nunk, Naperville, Ill.), and incubated in a 5% carbon dioxide gas incubator. Twenty four hours after the start of incubation, the medium was changed to the fresh medium without serum. After incubating for further 48 hours, the resultant was subjected to immunostaining according to the procedure described above.

(2) Results

Interleukin-8 was found to be distributed in theca cells of ovaries before and after ovulation. The intensity of staining was increased by hCG administration. The distribution of interleukin-8 in a ovarian follicle was not clear. In response to the growth of the ovarian follicle, the growing follicle was locally stained at the interleukin-8 distribution sites in the theca cell layers. Theca cells in an immature ovary of a rat were incubated in the absence of serum in order to examine whether or not interleukin-8 is produced in an immature ovary. As a result, interleukin-8 was found to be present in the supernatant by ELISA and SDS-PAGE analysis. Interleukin-8 was revealed to be locally present especially and mostly in the cytoplasm by histological observation.

The above-described results obviously show that ovarian endogenous interleukin-8 plays an important role on normal ovum growth, and that the theca cells can reliably be considered as cells producing endogenous interleukin-8.

Industrial Applicability

According to the present invention, leukocyte chemotactic factors have been revealed to have proconceptive activities. In addition to promoting activities for ovum maturation and ovarian follicle growth, such factors also exhibit activities of promoting implantation of the fertilized ovum onto the endometrium. Accordingly, it has been shown that such factors can be used in drugs or treatment agents in relation to medical treatment for infertility and artificial insemination in human beings and animals.

We claim:

1. A proconceptive method comprising administering interleukin-8 or monocyte chemotactic and activating factor in an amount effective to increase implantation of fertilized ovum or to promote maturation of unfertilized ovum.

* * * * *